(12) United States Patent
Siegel (10) Patent No.: US 6,537,577 B1
(45) Date of Patent: Mar. 25, 2003

(54) METHOD OF PROPHYLAXIS FOR BOVINE MASTITIS

(75) Inventor: Gregg Andrew Siegel, San Antonio, TX (US)

(73) Assignee: Bio Medical Development Corporation, San Antonio, TX (US)

( * ) Notice: Subject to any disclaimer, the term of this patent is extended or adjusted under 35 U.S.C. 154(b) by 0 days.

(21) Appl. No.: 09/873,633

(22) Filed: Jun. 4, 2001

(51) Int. Cl.[7] ................................................. A61K 9/14
(52) U.S. Cl. ....................... 424/486; 424/487; 424/484; 424/438; 424/405; 514/772.1
(58) Field of Search ................... 424/405, 438, 424/484, 486, 487; 514/772.1

(56) References Cited

U.S. PATENT DOCUMENTS

| | | | | |
|---|---|---|---|---|
| 4,113,854 A | * | 9/1978 | Andrews et al. | 424/81 |
| 4,309,328 A | * | 1/1982 | Carson | 260/29.6 |
| 4,434,181 A | * | 2/1984 | Marks, Sr. et al. | 424/326 |

\* cited by examiner

*Primary Examiner*—Thurman K. Page
*Assistant Examiner*—Liliana Di Nola-Baron
(74) *Attorney, Agent, or Firm*—John Lezdey (57) ABSTRACT

A method is provided for treating bovine mastitis by applying a porous strippable polymer film containing a medicament to the udders of the bovine.

14 Claims, 3 Drawing Sheets

METHOD OF PROPHYLAXIS FOR BOVINE MASTITIS

FIELD OF THE INVENTION

The present invention relates to a method of preventing bovine mastitis. There is also provided a method for treating cows, which have already been affected.

BACKGROUND OF THE INVENTION

Mastitis remains the most prevalent and persistent disease of dairy cattle. This disease is an inflammatory reaction of the mammary gland associated with a response to the presence of infecting pathogens. Although the disease is obvious upon direct observation in its clinical form, sub-clinical mastitis is more prevalent than clinical mastitis, since it usually precedes the clinical form and is more difficult to detect, the disease may become a prolonged infection and more difficult to overcome. Furthermore, the sub-clinical form of mastitis involves the presence of colonies of microorganisms that can lead to cross contamination and infection in other animals within the hood. The teat canal is the portal of entry for mastitis pathogens into the mammary gland. Lesions on the teats, particularly at the apex, contribute to increased incidence of infection.

A common cause is the attraction of insects such as flies to lactating cows which carry pathogens.

Economics losses from reduced milk production and the poor quality of milk product due to mastitis alone are estimated to be more than one billion dollars in the United States. Further, the losses are escalated to an additional billion dollars if the cost of antibiotic treatment and discarded milk is factored into the overall economic analysis.

Procedures to reduce the incidence of the mastitis disease include the use of effective pre-milking hygiene, the correct use of functionally adequate milking machines, the sanitization of teats after milking, the dry cow-treatment of all quarters of all cows, the prompt treatment of clinical mastitis and the culling of cows with chronic mastitis.

It has long been known to use disinfecting compositions to reduce or substantially eliminate mastitis-causing pathogens and microflora. Generally, such formulations are based on antimicrobial agents selected from chlorhexidines, iodophors, sodium chlorite-lactic acid compositions, sodium hypochlorite and hypo-chlorous acid. Iodophor preparations have been commonly used for this purpose. Though most of these germididals are effective against common mammary pathogens, many are not completely effective due to the lack of germicidal persistence throughout the intermilking period.

U.S. Pat. No. 4,288,428 issued to Foll and Widell disclose an iodophorus udder disinfecting composition comprising an alkylphenoxylpoly (ethyleneoxcy)ethanol-iodine complex or a polyvinylpyrrolidone-iodine comples used in solution form to treat the teats of the udders to yield a sufficient bacterial effect. These complexes dramatically reduced the noxious toxic properties of elemental iodine, i.e., the chaffing and etching of the udders and teats while preserving the broad germicidal spectrum of elemental iodine. Despite the advances provided by such iodophor complexes resulting in the reduction of detrimental effects of elemental iodine, side reactions may occur and release free elemental iodine from the solution.

Further, anionic and non-ionic surface-active components in formulations tend to remove protective fats and oils from the skin. These formulations, as well as, current teat disinfecting preparations have several glaring deficiencies in that these compositions do not provide a barrier film to prevent infection and to provide an extended delivery system for an antimicrobial agent and/or other medicaments to promote healing.

Therefore, there exists a need in the diary industry to provide a thin, tough, flexible, elastic film coating, which is skin adherent, adapts very well to all skin movements, yet provides a breathable, pinhole-free microporous structure that enables antimicrobial compounds to be incorporated therein and released over extended periods of time to prevent intramammmary infection between milking operations.

U.S. Pat. No. 6,139,856 to Kaminska, et al discloses a film forming composition suitable for use as a combination surgical skin preparation and drape. Another feature is the film's ability to serve as a vehicle for delivery of an antimicrobial agent and medicament to the skin surface. The film forming composition comprises a polymer mixture, including a polyvinylidene difluoride polymer, an acrylic polymer emulsion and an amine-substituted acrylic polymer, a specific amount of water, an effective amount of an antimicrobial liquid and an organic solvent for dissolving all components.

There is no suggestion in the patent that the disclosed composition could be used as a disinfecting preparation for the teats of udders of milk cows. Further, the patented composition is described (col. 4, lines 62–63) as having a resistance to physical removal, whereas the present method requires a film forming composition to be strippable prior to the milking operation. The present invention discloses a method which satisfies the many above-stated requirements by making unforeseen improvements by forming adherent teat coatings which disinfect the teat and provide a pinhole-free antimicrobial barrier that will protect the teat including crevices and fissures in the cutaneous tissue of the cow's teats. Ultimately, the method improves the quality of milk, reduces the costs associated with the antibiotic treatment and reduces the cost of milk to consumers.

SUMMARY OF THE INVENTION

In accordance with the present invention, a method of treating and preventing bovine mastitis has been found, employing a composition of matter to prevent infection of animal tissue and to prevent the transmission of mastitis pathogens to others.

In general, a method according to the invention comprises applying a microbicidal topical film-forming polymer coating composition to the teats of the udders, allowing the evaporation of the solvent to form a thin, tough, flexible, elastic coating, which is skin adherent, adapts very well to all skin movements, yet provides a breathable, pinhole-free microporous structure that retains an antimicrobial compound and allowing the film to remain on the teat surface for releasing the microbicidal over an extended period to afford persistent protective and/or treatment throughout the period between milking operations, i.e., the intermilking period. The microporous matrix of the protective barrier film coating prevents interference with the respiratory process of the treated teats. The resulting film adheres to the skin, which adapts well to all skin movements. Furthermore, the film while durable may be easily strippable with dry towels prior to milking operations. Advantageously, a dye or colorant is used in the composition to detect pinholes.

In its broadest aspect, the method of the invention is defined below.

A method of prophylaxis and treatment for bovine mastitis by forming a thin, flexible, microporous and strippable polymer coating having a physiologically active agent incorporated therein which is effective against mastitis-causing organisms, comprising the steps of:

A. applying a film-forming polymer composition to the teats of the udders, said composition comprises:
   (a) about 5 to 25 weight percent, based on the weight of the total composition of a film-forming mixture of:
      (1) about 30 to 60 weight percent of solids of a polymer of polyvinylidene difluoride;
      (2) about 10 to 25 weight percent of solids of an aqueous acrylic emulsion; and
      (3) about 10 to 30 weight percent of solids of an amine-substituted acrylic polymer;
   (b) about 5 to 40 weight percent of solids of a physiologically active agent; and
   (c) about 85 to 95 weight percent of a fugitive polar organic solvent; and B. allowing said fugitive solvent from the applied film-forming composition to evaporate and form a thin, flexible adherent, pinhole-free barrier film on the cutaneous tissue of the teat; and C. allowing said film coating to remain on the teat for releasing said physiological agent over an extended period to substantially eliminate the environmental and contagious organisms to provide prolonged, persistent protection against re-infection A preferred method of prophylaxis for bovine mastitis by forming a thin, flexible, microporous polymer coating having a physiologically active agent incorporated therein to provide prolonged persistent protection against mastitis-causing organisms, comprising the steps of:

A. applying a microporous film-forming polymer composition to the teats of the udders, said composition comprises:
   (a) about 10 weight percent, based on the weight of the total composition of a film-forming mixture of:
      (1) about 50 weight percent of solids of a copolymer of vinylidene difluoride and tetrafluorethylene;
      (2) about 25 weight percent of solids of an aqueous acrylic emulsion comprising a copolymer of methyl meth-acrylate, butyl acrylate and acrylic acid; and
      (3) about 25 weight percent of an amine-substituted acrylic polymer;
   (b) about 5 weight percent chlorhexidine diacetate; and
   (c) about 85 to 90 weight percent acetones.

B. allowing the acetone solvent from the film-forming composition to evaporate and to form a thin, flexible, microporous, pinhole-free, strippable polymer film; and C. allowing said film to remain on the teat for releasing said chlorhexidine diacetate over an extended period of time to substantially eliminate environmental and contagious organisms and to provide prolonged, persistent protection against re-infection.

It is, therefore, a primary object of this invention to provide a method of prevention or treatment of bovine mastitis to prevent intramammary infection and transmission of mastitis-causing organisms.

Another object of this invention is to provide a method for imparting continuous and prolonged delivery of an antimicrobial agent and prevent microbial rebound growth on the teat surface during the intermilking period.

A further object of this invention is to provide a method including a topical application to the teat to form a polymer film substantially free of pin holes to yield a barrier against mastitis-causing organisms and a microporous structure having antimicrobial compounds incorporated therein for sustained release to the teat.

Yet another object of this invention is to provide a method of prophylaxis of bovine mastitis by applying a film-forming polymeric composition containing a microbicidal agent including a colorant or dye to detect pinholes in the film.

A still further object of this invention, is to provide a method to provide a low-cost and effective long-lasting control of mastitis-causing organisms.

Still another object of the present invention is to provide a method to improve the quality and production of milk and ultimately reduce the cost of milk to the consumer.

These, together with other objects of the invention, along with the various features of novelty which characterize the invention, are pointed out with particularity in the claims annexed to and forming a part of this disclosure. For a better understanding of the invention, its operating advantages, and the specific objects attained by its uses, references should be had to the accompanying drawings and descriptive matter in which there is illustrated preferred embodiments of the invention.

DESCRIPTION OF THE PREFERRED EMBODIMENTS

According to the present invention, the method of prophylaxis for bovine mastitis comprises the steps of applying a microbicidal topical film forming coating composition to the teats of the udder, the composition comprises a polymer mixture of a polyvinylidence fluoride polymer, an acrylic polymer, and an amine-substituted acrylic polymer, a microbicidal agent capable of being releaseably retained in the film-forming coating composition, each being soluble in a fugitive non-toxic polar organic solvent. After allowing the fugitive solvent to evaporate from the applied film-forming composition, a thin, tough, flexible, transparent film forms on the teat surface. The resulting film coating adheres well to the cutaneous tissue of the teats and adapts to all skin movements, yet is easily hand strippable, i.e., using paper towels. The film coating is sufficiently microporous to sustain the release of various physiologically active agents such as therapeutic and antimicrobial agents while not interfering with the skin surface's necessary respiratory processes. This breathability allows water vapor to be released from the skin, but since the film is a pinhole-free membrane, it provides a barrier film which prevents water in the liquid state, as well as environmental and contagious pathogens from reaching the skin. The film coating is capable of releasably retaining the therapeutic and the antimicrobial agent to substantially inhibit microbial growth on the skin surface. The film coating releases sufficient antimicrobial agent to substantially eliminate the microorganisms, normally present on the skin surface and continues to release the antimicrobial agent during the entire intermilking period and prevent microbial rebound growth and promote healing of the skin surface.

Thus, the film coating composition of the present invention protects the teat surface from chemical and mechanical damage, allows the teat skin to breathe, and to be capable of sustained delivery through the microporous structure.

The film-forming coating composition useful in the method of this invention comprises about 5 to 25 weight percent based on the weight of the total film-forming composition which includes a) a polymer mixture component comprising about 50 weight percent of solids of a polymer of polyvinylidene difluoride, b) about 25 weight percent of solids of an aqueous acrylic emulsion, and c) about 25 weight percent of an acrylic polymer and about 5 to 50 weight percent based on the weight of total film-forming composition of a physiologically active agent wherein each component is solubilized in about 25 to 95 weight percent of a fugitive non-toxic polar organic solvent, which is preferably acetone.

The film-forming coating composition useful in the present invention involves polyvinylidene difluoride/acrylic polymer formulations. The polyvinylidene difluoride is the critical component in the formulations. The polyvinyledene difluoride (PVDF) may either be a homopolymer or copolymer. However, the amount of comonomers should not exceed the amount which would affect the characteristic of the copolymer film.

Suitable copolymers include tetrafluoroethane and hexafluoropropylene. The greater the PVDF concentration, the tougher the coating and ease with which it separates from the skin. For application requiring flexibility, skin-adhesion and durability in a humid environment, it is preferable to dilute the PVDF component by altering the copolymer content or by combination with an acrylic, such as, alkyl (meth) acrylate. For the present invention, other halogen-based polyvinylidene homopolymers, such as polyvinylidene chloride (PVC) may also be utilized. For purposes of the present invention, a suitable range of PVDF is determined to be about 30 to 60 percent by weight of solids.

The aqueous acrylic copolymer component comprises acrylic monomers, such as methyl acrylate, ethyl acrylate, butyl acrylate, methyl methacrylate, propyl methacrylate, ethoxyethyl acrylate, methoxyethyl acrylate, methoxyethyl methacrylate, ethoxyethyl methacrylate, and the like. Preferred acrylic terpolymer dispersants include methyl methacrylate/butyl acrylate/acrylic acid, propyl methacrylate/butyl acrylate/acrylic acid, methoxyethyl methacrylate/butyl acrylate/acrylic acid and methyl methacrylate/2-ethylhexyl acrylate/methacrylic acid. The acrylic aqueous component comprises about 10 to 30 weight percent of solids of a polymer of acrylic monomers.

The amine-substituted acrylic polymer is prepared from monomers selected from a dialkylaminoalkyl (meth)acrylate, and a lower alkyl (meth)acrylate would provide a composition forming a protective barrier coating with substantial increases in skin-adhesion and durability.

Suitable dialkylaminoalkyl (meth)arcylates which can be used to prepare the amine-substituted acrylic polymer include N.N-dimethylaminoethyl (meth)arcylate, N.N-diethylaminoethyl (meth)arcylate, t-butylaminoethyl (meth) arcylate and active salts thereof. About 20 to 30 percent by weight the amine-substituted acrylic polymer to total solids content has been found suitable for the coatings of the present invention.

Suitable lower alkyl (meth)arcylates which can be used to prepare the amine-substituted acrylic polymer comprise those having 1 to 8 carbon atoms in the alkyl group such as methyl acrylate, ethyl acrylate, isopropyl acrylate, methyl methacrylate, propyl methacrylate, ethoxyethyl methacrylate, and the like.

A preferred range for the amine-substituted acrylic polymer in the composition useful in the method of this invention ranges from about 10 to 30 weight percent solids of the total polymer constituent.

The term "fugitive solvent" as used herein describes an organic polar solvent having an appreciable vapor pressure at temperatures between about 25° C. and 80° C. which completely dissolves the components and quickly evaporates to form a coating. The preferred solvent provides a drying time of less than one minute, and comprises neither film toughness, nor the microporous film morphology. Exemplary solvents include acetone, ethyl acetate and mixtures thereof. Most preferable of the solvents is acetone because of its excellent disinfectant qualities and its volatility provides a preferable drying time of less than one minute.

Physiologically active substances or medicaments, which can be incorporated into the coatings of the invention, include antibiotics, disinfectants, therapeutics such as an anti-inflammatory agent or an anti-viral agent, therapeutics, antimicrobials, antifungal agents and other preparations for external use in customary veterinary treatment. The medicaments are either intended to treat the teats on contact or to penetrate and diffuse gradually into the body. Suitable microbicidal agents include iodophors, chlorophenols, biguanides silver sulfadiazine, chlorhexadine acetate, chlorhexadine and the like. The preferred microbicidal agent is chlorhexidine, which provides the desired microbicidal activity without altering film integrity or the microporosity. The concentration range of these physiologically agents range from about 0.5 to 25 weight percent. The preferred amount of chlorhexidine is about 5.0% w/w solids content.

The following examples illustrate the invention. The parts and percentages and ratios are on a weight basis unless otherwise specified.

EXAMPLE 1

A composition for forming a microporous film was prepared as follows utilizing commercially available compositions.

| Component | Weight |
|---|---|
| Kynar 7201 ® | 5 g. |
| Rhoplex BJ-15 ® | 2.5 g. |
| Eudragit E 100 ® | 2.5 g. |
| Acetone | 90 g. |

The preparation of the composition is performed at room temperature with an anchor stirrer. The listed components are sequentially placed into a beaker, and the composition thoroughly mixed by stirring overnight to prepare a 10% by weight of polymer solids composition.

EXAMPLE 9

Following the procedure of Example 1, to the resulting 10% by weight of polymer solids, 5% by weight chlorhexidine acetate was added to produce a film-forming composition with microbicidal activity.

TABLE 1 chemically identifies and describes commercially available sources of the components used in the examples.

TABLE I

| Ingredient | Product Identification | Source |
|---|---|---|
| Vinylidene Fluoride - Tetra Fluoroethylene Copolymer | Kynar 7201 | Elf Atochem ATO Philadelphia, PA |
| Acrylic Copolymer | Rhoplex B-15J emulsion | Rohm and Haas Company Philadelphia. PA |
| Butymethacrylate.2-Dimethylamino-ethyl Methacrylate and Methyl Methacrylate Acrylic Copolymer | ®Eudragit E100 | Hulls America, Inc. Somerset, NJ |
| Acetone | | Mallinckrodt Baker Inc. Paris KY |

In addition to the 10 weight percent of polymer solids composition prepared in Example 1, the solids components of the coating formulations were varied as a percentage of total weight within the liquid formulation. To evaluate the coating properties and to characterize their effectiveness as teat dips, coatings were evaluated at 8%, 10% and 20% w/w of the total solution.

Generally, a higher solids concentration (15–20% w/w) translates into coatings that are more easily removed and, by their physical thickness, provide a tougher film than those of a lower solids concentration. However, coatings formed from a higher solids content are not as flexible as those from lower solids content and are tighter on the skin. This results from the mechanism by which the coatings form on the skin, as the nascent film tends to shrink upon drying. Conversely, the lower solids content formulations (8–12% w/w) are more comfortable, but due to being very thing, may be more difficult to remove and may not offer as tough of a coating as those from the higher solids compositions. The solids content, and thus the above properties, were adjusted by varying the dilution with acetone. These base formulations were then further altered to include colorants and germicides.

Preferably, the composition is composed of a solids content of about 5 to 10% by weight, providing suitable films with a thickness of about 0.010 mm to 0.015 mm when applied in single coatings to the teat surface.

The teat coatings are inherently transparent and therefore difficult to observe after applied. The addition of color to the coatings is an important characteristic enabling the observation of the integrity of the coating material, and ensuring that the coating is completely removed prior to milking to prevent blockage of in-line milk filters. Furthermore, the ability to readily detect the durability of coatings serves as a visual assurance of antimicrobial persistence throughout the intermilking period. The following Food, Drug and Cosmetic approved dyes were incorporated in the formulation at approximately 0.1%. Suitable dyes include Drug and Cosmetic Green No. 6, Red No. 17, Violet No. 2, Yellow No. 11 and Orange No. 5. For teat coatings, Violet No. 2 and Green No. 6 are most preferred.

The integrity of the coating material insures pinhole-free film as not to violate the protective barrier characteristic of the teat dip.

It is a feature of the present invention that the method produces film-forming coatings that provide a protective barrier against water, environmental and contagious pathogens, as well as, carriers of appropriate microbicidal effects. The first step of the present method involves applying the PVDF polymer/aqueous acrylic copolymer emulsion/amine-substituted acrylic copolymer/medicament/acetone system to the teats of the udders of a cow by either dipping, brushing, spreading or spraying. In most cases, dipping is preferred. After the application is completed, the next step is to allow the solvent to evaporate to form a film with sufficient microporosity for both maintaining the skins' respiratory processes and supporting the release of an encapsulated medicament. These films produced from a mixed solvent system such as the formulations described above, form phase-inversion membranes. Phase-inversion membranes are solvent-cast films in which two liquid phases form and produce a stabilized gel prior to complete solvent depletion. In the present case, as the acetone evaporates, the relative proportion of the less volatile, nonsolvent component (i.e., water—from the acrylic emulsion) increases and eventually causes the polymer to separate into a polymer-rich phase dispersed in an acetone-rich phase. Films that form under these circumstances as noted have a microporous structure and for the purpose of treating teats should be substantially pinhole-free. Such evaporation generally occurs in less than one minute. Preferably a dye or colorant is used in the composition to provide the means to visually inspect if the teat was adequately covered and if the film is pinhole-free. After forming the film must adapt well to all the teat and udder movements, and be free of pinholes, wrinkling, tearing, lifting or bubbling.

The invention is further illustrated by the following evaluations and studies.

In the following formulations, the weight percentages of the solids components of the coating compositions are based on the polymer solids of EXAMPLE 1 and were varied as a percentage of the total weight within the liquid formulation.

TABLE II

| FORMULA NO. | SOLIDS wt % | CHX wt % | GREEN NO. 6 wt % |
|---|---|---|---|
| 1 | 8 | — | — |
| 2 | 8 | 6.0 | — |
| 3 | 10 (EX 1) | — | — |
| 4 | 10 | — | 0.2 |
| 5 | 10 (EX 2) | 5.0 | — |
| 6 | 10 | 5.0 | 0.2 |
| 7 | 20 | — | — |
| 8 | 20 | 2.6 | — |

Adhesion-removal Evaluations

Formula No 4

Ten lactating cows with normal, healthy teats were selected randomly from the milking herd of the Hill Farm Research Station, and used in the 1-week trial. Immediately after milking, all teats of each cow were dipped full length in the above formulation by the milking machine operator.

After the coating was allowed to dry, cows were moved to an open pasture and dirt lot for approximately 12 hours where they had access to food and water as well as the opportunity for exercise. Immediately prior to the next milking, teats were briefly immersed into a 2.5% acetic acid solution (predip) and allowed to drain for 30 seconds to aid in the removal of the thin film product.

Visual observation of the 10% solids formulation indicated that substantially all of the formed film remained on teat surfaces during the intermilking period. The remaining thin film could be removed after dipping in acetic acid, allowing a 30 second contact time and removing the film coating by wiping with a dry paper towel. Observations on the lateral teat surfaces and orifices indicated no adverse effect of the thin film or acetic acid dip, such as chapping, scaling, or hyperkeratosis; all teats were classified as normal in appearance.

Although subjective in nature, this trial suggested that the 10% solids coating formulation has adequate adherence to teats during the intermilking period (when the cows are exposed to mastitis-causing bacteria), is easily removed using 2.5% acetic acid as a pre-milking teat dip, and is nonirritating to the teats.

8% solids & 20% solids Test

A simulated test was performed on five dairy cows to verify the ability of two formulations to form a coherent coating on teats, to remain intact during the intermilking period and to be removed in the pre-milking period.

Five lactating cows with normal, healthy teats were selected randomly from the milking herd of the Hill Farm Research Station. Immediately after milking, the right front and left rear teats of each cow were dipped in 8% polymer solids content formulation; the left front and right rear teats were dipped in a 20% polymer solids formulation. Dipping was performed by a milking machine operator. After the coating dried, cows were moved to a concrete holding area equipped with a chute and head gate. Cows were held in this area for 12 hours until the next milking for observation. At hourly intervals, starting at 5:00 AM, cows were placed into the chute and teats were scored to determine percentage adherence of the two coating formulations. After assessment of adhesiveness and prior to the next milking, teats were briefly immersed into a 2.5% acetic acid solution and allowed to drain for 30 seconds to aid in the removal of the coating products. The film remaining on teat surfaces after the intermilking period was removed after dipping in acetic acid, allowing a 30 second contact time, and removing the thin film by wiping with a dry paper (cow) towel.

Figure 1:
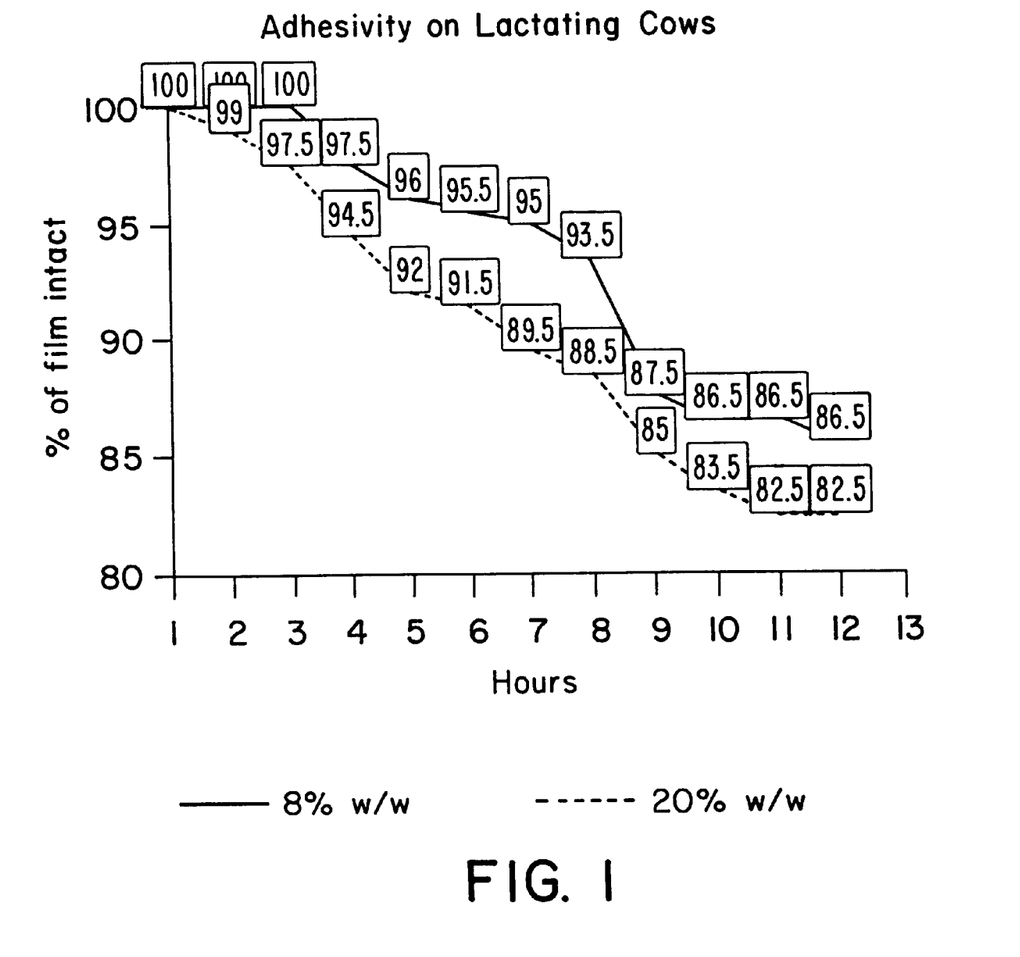
FIG. 1 illustrates that the method of the present invention provides a coherent pinhole-free coating on the teats of lactating cows which remain intact for a long period of time. The figure also shows that the teat adherence is slightly greater for the lower amount of solids in the film-forming composition.

On average, at least 83% of the teat surface remained covered by both of the test products by 12 hours which was just prior to the next milking (See FIG. 1). Adherence appeared slightly greater for the 8% solids formulation compared with the 20% formulation at 3 hours after milking, and this trend continued through 12 hours.

Both the 8% solids and 20% solids formulations were more difficult to remove than the 10% formulation previously tested. It is desirable that all of the coating composition should be removed from teats to prevent build-up and blockage of the in-line milk filter with the film composition. Thus, during the pre-milking hygiene procedure, all remaining thin film was removed.

However, it was estimated that, even after the acetic acid dip followed by the paper towel wipe, approximately half of the 20% solids product had to be manually removed using the fingers, and approximately one-fourth of the 8% solids formulation had to be similarly removed. It should be noted, however, that the 20% solids coating was much easier to view on teat surfaces compared with the 8% product; so this observation may have biased results, i.e., it was difficult to estimate the remaining 8% coating because it was more difficult to visualize. This re-emphasizes the need to include a dye or colorants in the coating formulations.

Adherence was better using the 8% formulation maintaining greater than 95% coverage for 7 hours than greater than 85% coverage for the last 5 hours. Both the 8% and 20% formulations were more difficult to remove than the 10% formulations previously studied. Reasons why the 8% and the 20% products were difficult to remove are unclear, however, when the 10% product was being evaluated, cows were held in an open pasture and dirt lot, they had the opportunity for exercise, and cows were observed laying down at times. When the 8% and 20% formulations were tested, cows were held in a small concrete holding pen, did not have the opportunity for exercise, and did not lay down. It is believed that cows that were dipped in the 10% formulation with access to pasture, dirt lots, and exercise (which simulated natural holding conditions) had greater exposure to the elements, which would have been abrasive to teats, loosened the 10% solids, and allowed easier removal.

PVDF 1 acrylic copolymer coatings demonstrated adequate adherence properties necessary to provide protection throughout the intermilking period.

Microporosity

Moisture Vapor Transmission Rate

Microporosity is an essential feature of the film coatings useful in the method of the present invention. The moisture vapor transmission rate (MTVR) is the measurer of a film's ability to allow air and water vapor to pass through while preventing the passage of water in the liquid state. The MTVR is directly related to the microporous morphology of a film, and is defined by the presence of pores extending throughout the film. The film coatings of the present invention provide a physical barrier to moisture (liquid) while allowing moisture vapor to permeate through. The microporosity, and thus, the MTVR of the film coatings of the invention can be varied over a wide range of compositional variations. When examined under an electron microscope at 500× to 5,500×, a composition coating prepared in EXAMPLE 1 was found to have pores of about 0.5 to 1.0 wm (microns) in diameter.

In accordance with the procedures of EXAMPLE 1 and EXAMPLE 2, PVDF/acrylic copolymer films were prepared. The MVTR of films of various formulation was conducted in two groups. The first group included formulation having 8.0%, 10% and 20% solids without either antimicrobial or dye. The second group involved 10% solids and 5.0% chlorhexidine (EXAMPLE 2); 10% solids, 5.0% chlorhexidine and 0.2% FDC Green No. 6; and 20% solids and 2.6% chlorhexidine.

As shown in TABLE II for specific formulations above. Thin films were prepared by dipping a plastic sheet in thin film formulations and were allowed to dry. Two samples were obtained for each formulation. The film was stretched and secured over the mouth of 28.5 mm diameter disposable centrifuge tube which was filled with 30 grams of 0.8% Na Cl solution. The tubes were kept inverted to maintain contact between the solutions and the film and to check any leakages for 30 minutes at room temperature. The weight of each tube was recorded at room temperature. The weight of each tube was recorded and the tubes were placed in an incubator maintained at 37° C. The amount of water due to evaporation was monitored over 72 hours.

Figure 2:
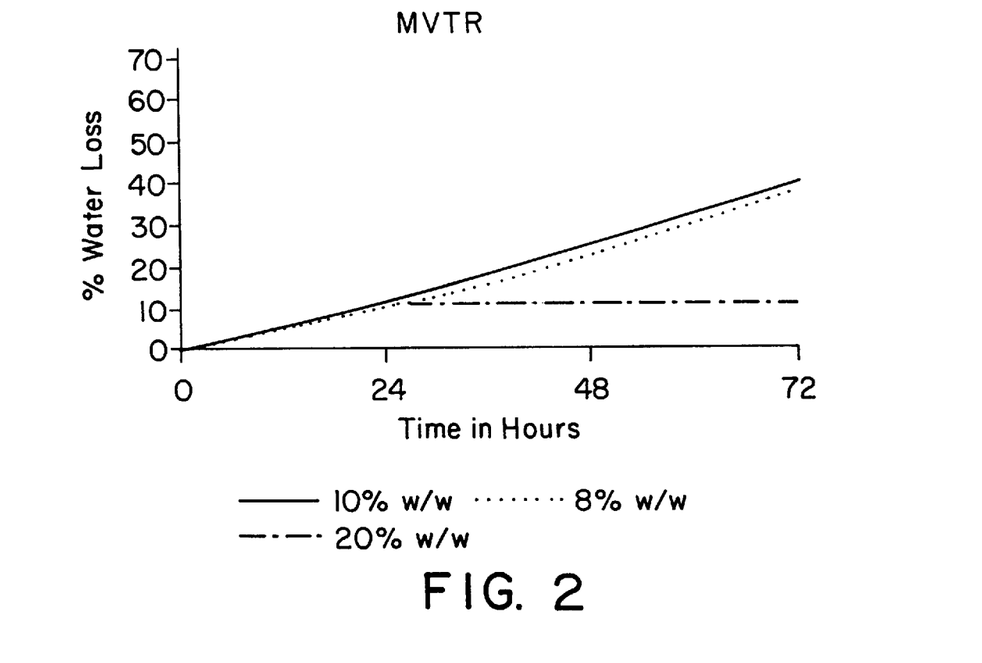
FIG. 2 illustrates that the Moisture Vapor Transmission Rate (MTVR) for film coatings useful in the method of the present invention. All thin films used in the method transmitted vapor and the films with chlorhexidine and/or dye had higher transmission rates.
Figure 3:
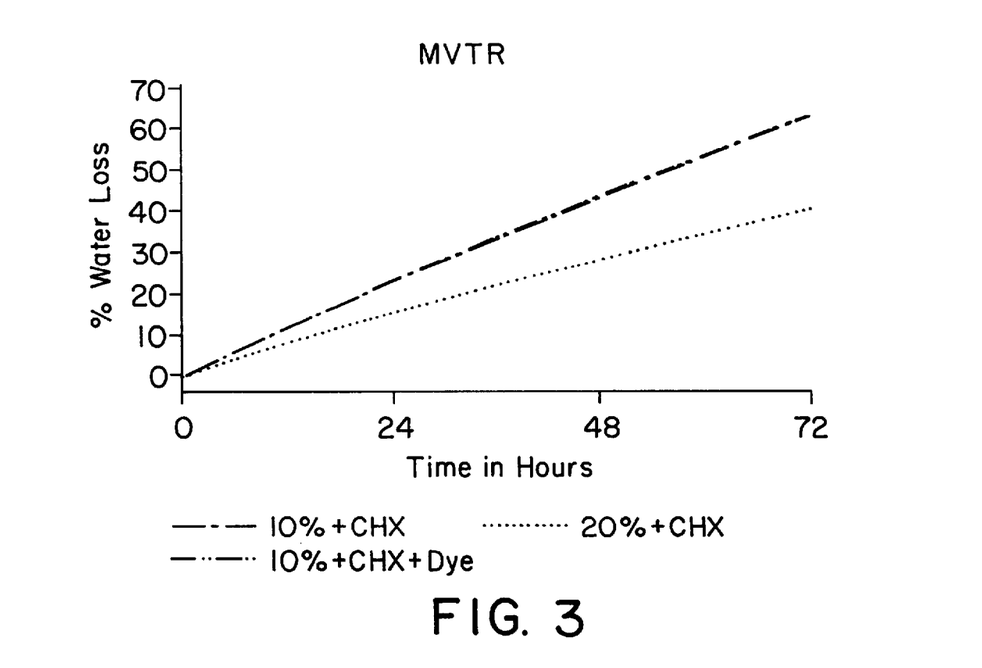
FIG. 3 shows that thin films with chlorhexidine and/or dye had higher vapor transmission than films without the antimicrobial agent.

As shown in FIG. 2, the MTVR of different solids varies and as expected, the higher solids content demonstrates less vapor transmission. FIG. 3 shows that the addition of chlorhexidine increases vapor transmission when compared to the formulations without the antimicrobial loadings. Further, these results indicate that the microporous framework of the PVDF/acrylic copolymer film-forming coatings enables various physiologically active substances such as various therapeutic or antimicrobial compounds to be incorporated into the coating and released to contact the surface of the teat.

Sustained Release Study

Release of Chlorhexodine from PVDF/Acrylic Copolymer Coatings

Sterile 60×15 mm glass petri dishes were coated with 0.5 ml of a formulation of EXAMPLE 2 with 0.2 wt % D & C Green No. 6 dye. Three samples for each time point were prepared. A control sample with 10% thin film only was also prepared for each time point. A 3 ml volume of sterile d-water was added over the dry film and the petri dishes were covered and incubated at room temperature for 8 hours. The 3 ml volume of water was removed from each dish after 5 min., 1, 2, 3, 4, 5, 6, 7, and 8 hours and placed in a sterile 15 ml conical tube with cap.

A standard curve was obtained using d-water containing 0 (blank), 1, 2, 3, 4, 5, 6, 7, 8, 9, 10, 15, 20, 25 and 30 &g/ml of chlorhexidine acetate. The samples from each time point were read on the spectrophotometer at $A_{254mm}$. The 10% thin film control reading was subtracted from each set of sample averaged time points and the sample readings converted to &g of chlorhexidine by reference to the standard curve (calibration graph).

The biological activity was determined using *Staphylococcus aureus* (ATCC 29740), a pathogen associated with bovine mastitis. A standard inoculum was prepared by transferring colonies from a fresh subculture of the test organism on 5% sheep blood agar to sterile d-water to a McFarland standard 0.5. A 1:100 dilution of the bacterial suspension was made in sterile d-water which is equal to a concentration of $1-1.5 \times 10^6$ cfu/ml.

Antibacterial activity of the chlorhexidine released into the water was determined by performing minimum inhibitory/bactericidal concentration (MIC/MBC) assays. For each time point, a series of 2-fold dilutions was prepared in Mueller Hinton (MH) broth and added to an equal volume of the test organism, *Staphylococcus aureus* (ATCC 29740; $\sim 10^6$/mL). Tubes were incubated at 37° C. for 24 hours and then assessed for turbidity. The tube with the highest dilution that was not turbid was recorded as the MIC.

A 0.1-mL volume from nonturbid tubes was subcultured on M H agar, incubated at 37° C. for 24 hours, and assessed for growth. The highest dilution tube that had no growth was recorded as the MBC. A control tube (broth and the test organism) was incubated and was used to verify growth of the test organism.

Figure 4:
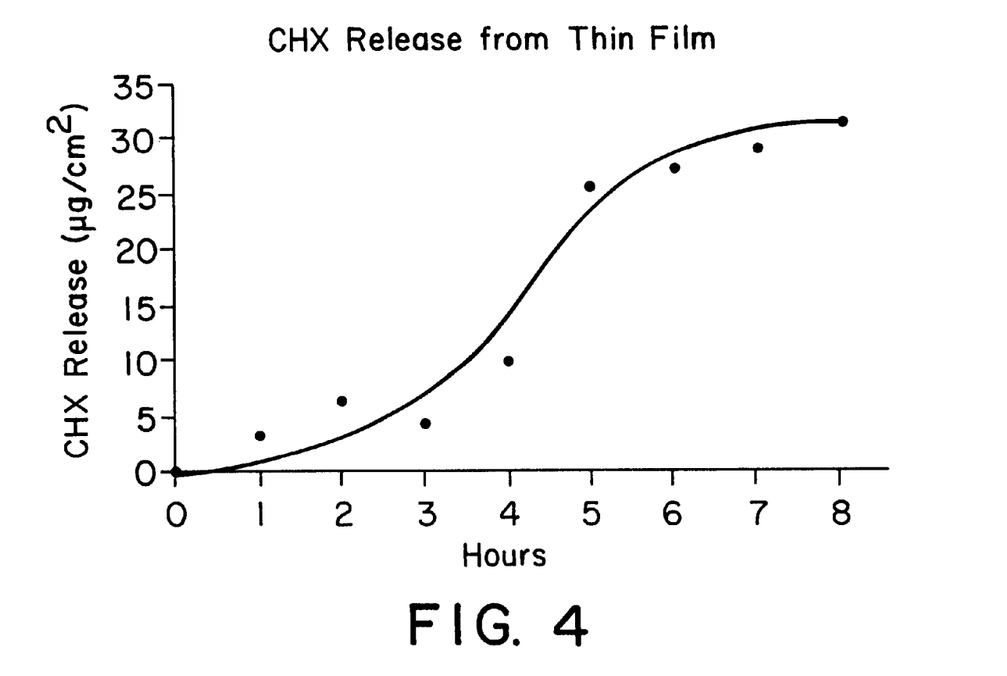
FIG. 4 illustrates that chlorhexidine is released from the thin films used in the present method in a sustained manner over time to offer persistent protection against mastitis pathogens.

The MIC and MBC data is shown in TABLE IV and FIG. 4.

TABLE III

Minimum Inhibitory and Minimum Bactericidal Concentrations of chlorhexidine released from 10% (w/w) solids formulations

| Time (hr) | Germicide Released (&g/cm²) | MIC | MBC |
| --- | --- | --- | --- |
| 0 | 0.11 | <1:2 | <1:2 |
| 1 | 3.3 | 1:8 | 1:4 |
| 2 | 6.4 | 1:8 | 1:2 |
| 3 | 4.5 | 1:16 | 1:4 |
| 4 | 10.1 | 1:16 | 1:4 |

TABLE III-continued

Minimum Inhibitory and Minimum Bactericidal Concentrations of chlorhexidine released from 10% (w/w) solids formulations

| Time (hr) | Germicide Released (&g/cm²) | MIC | MBC |
| --- | --- | --- | --- |
| 5 | 25.8 | 1:32 | 1:8 |
| 6 | 27.4 | 1:32 | 1:8 |
| 7 | 29.3 | 1:64 | 1:4 |
| 8 | 31.7 | 1:64 | 1:8 |

Results demonstrate that chlorhexidine is released from the thin film, providing sustained antimicrobial activity that should continue throughout the intermilking period providing protection against mastitis pathogens.

Microbicidal Efficacy Study

To evaluate the microbicidal activity of the compositions of EXAMPLE 1 and EXAMPLE 2, basic excised teat models used for these experiments are based on providing procedures by Twomey, A, and M. A Arnold, National Dairy Lab. Report, Ruaburn Agric. Res. Center, Hamilton, New Zealand.

Excised Teat—Preliminary Trial Organism: *Staphylococcus aureus*

Teats used for the in vitro assay were collected from slaughtered dairy cows, and those were discarded that exhibited rough skin, chaps, or abrasions. Excess skin and tissue were trimmed, teats were washed in a mild detergent and warm water, rinsed in water, dried, and dipped in 70% ethyl alcohol. Teats were placed in plastic bags in a glycerin and water solution, and subsequently frozen at −20° C. until further use. Frozen teats were thawed in warm water, rinsed in water, dried, and dipped in 70% ethyl alcohol, dried with paper towels, and suspended by metal clips from a glass rod.

The pathogen strain that was used for this study was *Staph. aureus* ATCC 29740. For preparation of *Staph. aureus*, five 6-ml tubes of trypticase soy broth (TSB) (Becton Dickinson, Cockeysville, Md.) were inoculated from a culture of *Staph. aureus* actively growing on trypticase soy agar (TSA) (Becton Dickinson) containing 5% bovine calf blood. These tubes were incubated for 5 to 7 hours at 37° C., and this culture was used to inoculate 250 ml of TSB, which was incubated on a gyratory shaker for 16 hours. After incubation, bacterial cells were pelleted by centrifugation at approximately 7000×g, washed twice in 0.1% proteose peptone (Difco Laboratories, Detroit, Mich.), and resuspended to approximately 200 ml in proteose peptone. Serial dilutions were prepared in proteose peptone, and 0.1 ml was plated on TSA. Plates, were incubated for 24 hours at 37° C. and colonies were counted to determine the microbial concentration of the stock suspension.

The dilution required to prepare a challenge inoculum of approximately $1 \times 10^8$ colony-forming units (cfu)/ml of *Staph. aureus* was calculated from results of the standard plate counts. Challenge suspensions of *Staph. aureus* containing approximately $1 \times 10^8$ cfu/ml of each organism (diluted with pasteurized milk) were prepared and used for the excised teat trials. The quenching solution was letheen broth (Difco Laboratories) modified to contain 1% sodium thiosulfate (Sigma Chemical Co., St. Louis, Mo.).

Teats were dipped in a *Staph. aereus* bacterial suspension to a depth of 15 mm and allowed to drain for 5 minutes. Teats were then dipped into two coating formulations of EXAMPLE 1 and EXAMPLE 2, (Formula No. 3 and Formula No. 5, respectively) to a depth of approximately 30 mm and allowed to drain for 10 minutes. Following drainage, teats were dipped into 2.5% glacial acetic acid and allowed to remain for 1 minute to soften the material. The coating was then removed from each teat using a sterile cotton swab by rolling the edge of the softened film using a downward motion toward the teat apex, placed in 5 ml of quencher in sterile blood dilution vials (Baxter Diagnostics, McGaw Park, Ill.), mixed by vortexing for 5 seconds, and after serial dilution, a 0.1-ml aliquot was plated onto TSA. The quenching solution (Bacto-Letheen Broth) was used to inactivate the chlorhexidine germicide and prevent further bacterial killing upon culture. Immediately after the dried coating products were removed from the teats, each teat was rinsed to a total volume of 5 ml of quencher, the rinse collected in sterile blood dilution vials (Baxter Diagnostics) separate from the peelings, mixed by vortexing for 5 seconds, and after serial dilution, a 0.1-ml aliquot was plated to determine the number of organisms remaining on the teat after removal of the coating.

The preliminary trial demonstrated that the 2.5% glacial acetic acid softened the coatings, and that the coating could be successfully peeled from the teats. Evaluation of the 2.5% glacial acetic acid solvent in this preliminary trial against *Staph. aureus* revealed a log reduction (LR) in bacterial numbers of less than 1, i.e., 0.44 (Table 1), indicating a minimal effect of acetic acid on bacteria killing.

Plating of the coating peelings containing chlorhexidine yielded a 4.24 LR against *Staph. aureus* (Table V). Likewise, plating of the rinses of teats after coating removal yielded a LR of 4.49. It is expected that an effective teat germicide will achieve al least a 3, and preferably a 4 or 5 LR in the geometric mean of the recoverable bacterial population. Thus, the germicidal activity of the PVDF coating product was more than adequate.

The peelings of the PVDF/acrylic polymer coating (Formula No. 3) without chlorhexidine yielded a LR of 2.81 indicating that, with addition of chlorhexidine to the product, a much better kill of *Staph. aureus* was achieved. However, plating of the rinses of teats after removal of the coating without chlorhexidine yielded a LR of 4.25. The similar LR of 4.49 and 4.25 for the two PVDF/acrylic polymer coating products for rinses underneath the film may indicate that the action of peeling the films from teats eased the removal of bacteria. Whether all of the bacteria that were peeled from the teat and included in the peelings were recovered and plated after mixing with quencher is unknown. Additionally, if bacteria remain embedded in the coating peelings, it is unknown if these bacteria are viable organisms that would be capable of causing an intramammary infection in the live cow environment.

In a separate analysis of the preliminary trial results, the cfu of bacteria recovered from peelings and from rinses for the composition of EXAMPLE 2 (Table IV below) were combined and LR were determined. The same analysis was performed for the formulation EXAMPLE 1. The LR for the combined cfu for the PVDF (Formualtion No. 5) with chlorhexidine was 4.18, which is similar to the 4.24 value found for the peelings and to the 4.49 value found for the rinses. The LR for the combined cfu for the PVDF coating without chlorhexidine was 2.77, which was similar to the 2.81 value found for the peelings alone, but lower than the 4.25 value for the rinse alone.

The preliminary trial demonstrated that 2.5% glacial acetic acid softened the PVDF coating, and that the coating could be successfully peeled from teats. Glacial acetic acid had minimal effects on bacterial killing. The coating of EXAMPLE 2 resulted in a LR of 4.18, which was considered adequate germicidal activity, whereas the formulation without chlorhexidine resulted in a LR of 2.77, which was considered inadequate, but expected, because the product contained no germicide other than any antimicrobial components of the PVDF and the acrylic polymers. Based on these date, it was decided to evaluate only the coating of EXAMPLE 2 and to include peelings and rinses combined to determine recoverable cfu.

Results of this preliminary trial demonstrated that the modified excised teat trial was suitable for evaluating the germicidal activities of the coating formulations of EXAMPLE 2 on teat skin. Therefore continued testing was carried out as described below for the germicidal product.

TABLE IV

Excised Teat Study, Preliminary Trial, Organism: Staphylococcus aureus

| Treatment | Dilution | Count No. | Plate no. 1 | Plate no. 2 | Geometric Mean | Total organisms Recovered | Log | Log reduction |
|---|---|---|---|---|---|---|---|---|
| 2.5% acetic acid | −3 | 1 | TNTC[1] | TNTC | | | | |
| 2.5% acetic acid | −3 | 2 | TNTC | TNTC | | | | |
| 2.5% acetic acid | −4 | 1 | 460 | 262 | | | | |
| 2.5% acetic acid | −4 | 2 | 327 | 268 | 320.58[3] | 16,029,000 | 7.20 | 0.44 |
| 10% solids with 5% chx[2] peeling | −3 | 1 | 28 | 0 | | | | |
| 10% solids with 5% chx peeling | −3 | 2 | 23 | 0 | .50 | 2,500 | 3.40 | 4.24 |
| 10% solids with 5% chx rinse | −3 | 1 | 6 | 0 | | | | |
| 10% solids with 5% chx rinse | −3 | 2 | 10 | 0 | .28 | 1,400 | 3.15 | 4.49 |
| 10% solids without 5% chx peeling | −3 | 1 | 89 | 3 | | | | |
| 10% solids without chx peeling | −3 | 2 | 122 | 1 | 13.43 | 67,150 | 4.83 | 2.81 |
| 10% solids without 5% chx rinse | −3 | 1 | 22 | 0 | | | | |
| 10% solids without 5% chx rinse | −3 | 2 | 26 | 0 | .49 | 2,450 | 3.39 | 4.25 |
| Neg control | −4 | 1 | 1025 | 853 | | | | |
| Neg control | −4 | 2 | 742 | 880 | 884.26 | 43,213,000 | 7.64 | — |

[1] = Too numerous to count.
[2] = Chlorhexidine acetate.
[3] = Means within mw.

Efficacy of Formula No. 4 in Excised Teat Model

The thin film based on the formulation of EXAMPLE 2 and Green No. 6 dye (formula No. 4—TABLE II) was tested for germicidal activity using exposure to *Staphylococcus aureus* and *Streptococcus Agalactine*.

Teats were prepared as described earlier. The pathogen strains that were used for this study were *Staph. aureus* ATCC 29740 and *Strep. Agalactiae* ATCC 27956. A culture of *Strep. Agalactiae* was prepared by thawing a frozen vial of *Strep. Agalactiae* and plating on a TSA blood plate. After 24 hours incubation at 37° C., five 6-ml tubes of TSB were inoculated with approximately six colonies of *Strep. Agalactiae* each. These cultures were incubated at 37° C. for approximately 16 hours and then used to inoculate 250 ml of TSB. This culture was incubated on a gyratory shaker for approximately 5.5 hours. Serial dilutions were prepared in proteose peptone, and 0.1 ml was plated on TSA. Plates were incubated for 24 hours at 37° C. and colonies were counted to determine the microbial concentration of the stock suspension.

The dilution required to prepare a challenge inoculum of approximately $1 \times 10^8$ colony-forming units (cfu)/ml of *Staph. aureus* or *Strep. Agalactiae* was calculated from results of the standard plate counts. Challenge suspensions of *Staph. aureus* and *Strep. Agalactiae* containing approximately $1 \times 10^8$ cfu/ml of each organism (diluted with pasteurized milk) were prepared and used for the excised teat trials. The quenching solution was letheen broth (Difco Laboratories) modified to contain 1% sodium thiosulfate (Sigma Chemical Co., St. Louis, Mo.).

The following materials were tested: 1) film coating of EXAMPLE 2, 2) 2.5% glacial acetic acid, 3) a positive control (0.5% commercially available iodine teat dip, Theratec®, Babson Bros., Co., Naperville, Ill.), and 4) the negative control were tested in Trials 1 and 2 against *Staph. aureus* and *Strep. Agalactiae*, respectively. Ten teats were used for each trial to test each experimental product, the positive and negative controls, as well as the 2.5% acetic acid. Teats were dipped in the bacterial challenge suspensions once to a depth of approximately 15 mm and allowed to drain for 5 minutes, then dipped with the test products to a depth of approximately 30 mm and drained for an additional 10 minutes. For the challenged, but undipped negative control teats, the drainage time was 15 minutes. After the coating of EXAMPLE 2 was drained from the teats for 10 minutes and had dried, teats were dipped into 2.5% glacial acetic acid and allowed to remain for 1 minute to soften the coating film, and then the coating film was removed intact from each teat using a sterile cotton swab as described above. This coating film peeling from each teat was placed in sterile blood dilution vials (Baxter Diagnostics). Remaining organisms on teat skin were then removed by rinsing each teat with approximately 5 ml of quencher expressed from a polyethylene wash bottle into the same vial containing the coating film peeling. Each vial was vortexed for 5 seconds before plating.

In Trial 3, the excised teat model was modified to determine if the presence of the dried, intact film on teats exhibited microbicidal properties. Teats were dipped into the PVDF coating test products (with and without 5% chlorhexidine) to a depth of 30 mm, allowed to drain and dry for 5 min, and then immersed into a *Strep. Agalactiae* challenge suspension to a depth of approximately 15 mm and allowed to drain for 10 min. The challenge suspension was then rinsed into sterile vials and 0.1-ml aliquots were plated.

For all three trials, serial dilutions of peelings or rinses were made in 0.1% proteose peptone, and platinf was in 0.1-ml aliquots on Mannitol Salt agar (Becton Dickinson) for *Staph. aureus* and TKT/FC agar (Becton Dickinson) with 0.3% thallium acetate (Sigma Chemical Co.) for *Strep. Agalactiae*. Rinses from negative control teats required plating at $10^{-4}$ to achieve countable plates, while rinses from teats dipped with the test products were plated at $10^{-3}$ and $10^{-4}$. Plates were incubated for 24 hours at 37° C. and colonies were counted. The geometric mean count of the plates was determined, multiplied by 5 to express the total volume of rinse, and then multiplied by the dilution factor to yield the total cfu per teat. In cases in which no organisms were recovered from a teat, the value of 0.01 was substituted fro zero in order statistically determine the mean cfu counts.

The same set of teats was used for each trial. Between runs within a trial, teats were rinsed in warm water for 2 minutes with agitation, dried, rinsed in a 0.05% sodium thiosulfate solution for 1 minute, dried, rinsed in a solution containing 0.05% lecithin (Fisher Scientific, Fair Lawn, N.J.) and 0.05% Tween 80 (Fisher Scientific) for 1 minute, dried, rinsed in warm water for 1 minute, dried, dipped in 70% ethyl alcohol, dried, and resuspended to air dry.

In Trial 1, a LR of 4.55 was achieved with the Formula No. 4 coating with chlorhexidine against *Staph. aureus*, which was comparable with the 4.73 LR found with the positive control product (Table VI). The 2.5% acetic acid treatment exhibited some germicidal activity (LR 0.76) but was insignificant compared with the PVDF coating product with chlorhexidine.

In Trial 2, a LR of 4.47 was achieved with the Formula No. 4 with chlorhexidine against *Strep. Agalactiae*, which was greater than one LR higher than the 3.40 LR found with the positive control product (Table VII). The 2.5% acetic acid treatment exhibited some germicidal activity (LR 0.93), but as in Trial 1, was insignificant compared with the Formula No. 4 coating with chlorhexidine.

In Trial 3, in which the *Strep. Agalactiae* challenge suspension was applied over the PVDF coating experimental teal dip, the PVDF coating with and without chlorhexidine achieved a 0.17 and a 0.14 LR, respectively (Table VIII). This suggests that the exterior of the dried film on teats has little germicidal activity under the conditions of this assay.

The Formula No. 4 coating achieved LR of 4.55 and 4.47 against *Staph. aureus* and *Strep. Agalactiae*, respectively. These results compare favorably with previous trials using the conventional excised teat model[14] in which a 1% iodophor product achieved 5.61 and 4.43 LR against *Staph. aureus* and *Strep. Agalactiae*, respectively. In the same report[14], a 0.5% chlorhexidine gluconate product achieved LR of 3.22 and 2.92 against *Staph. aureus* and *Strep. Agalactiae*, respectively. Thus, the PVDF coating with chlorhexidine exhibited adequate germicidal activity when applied to teats challenged with bacteria.

The test was performed with similar results for *Staphylococcus epidermidis, Pseudomonas aeruginosa, Staphylococcus aureus, Proteus vulgans, Candida albicans, Serratia marcesens,* and *Trichophyton mentagrophytes*. The results of the test demonstrate that antimicrobial agents encapsulated within the improved PVDF-based coating of the present invention provide substantial microbicidal activity in vitro against a variety organisms.

TABLE V

Excised Teat Study, Trial 1, Organism: Staphylococcus aureus

| | | Count | Plate No. | | | | | | | | | |
|---|---|---|---|---|---|---|---|---|---|---|---|---|
| Treatment | Dilution | No. | 1 | 2 | 3 | 4 | 5 | 6 | 7 | 8 | 9 | 10 |
| 10% solids with 5% chx[1] EXAMPLE 2 | −3 | 1 | 28 | 0 | 4 | 0 | 3 | 0 | 0 | 0 | 2 | 0 |
| 10% solids with 5% chx[1] | −3 | 2 | 27 | 0 | 2 | 0 | 0 | 0 | 1 | 0 | 3 | 2 |
| 2.5% acetic acid | −4 | 1 | 138 | 44 | 56 | 257 | 139 | 12 | 147 | 91 | 130 | 145 |
| 2.5% acetic acid | −4 | 2 | 144 | 32 | 55 | 249 | 77 | 28 | 144 | 117 | −4 | 157 |
| Pos Control | −1 | 1 | 40 | 8 | 97 | 204 | 27 | 67 | 0 | 6 | 46 | 0 |
| Pos Control | −1 | 2 | 21 | 5 | 68 | 189 | 92 | 63 | 0 | 21 | 65 | 2 |
| Neg Control | −4 | 1 | 662 | 353 | 525 | 649 | 547 | 620 | 408 | 296 | 1808 | 248 |
| Neg Control | −4 | 2 | 598 | 403 | 589 | 516 | 526 | 488 | 377 | 352 | 1944 | 334 |

| Treatment | Geometric Mean | Total organisms Recovered | Log | Log reduction |
|---|---|---|---|---|
| 10% solids with 5% chx[1] EXAMPLE 2 | | | | |
| 10% solids with 5% chx[1] | 0.147[2] | 735 | 2.87 | 4.55 |
| 2.5% acetic acid | | | | |
| 2.5% acetic acid | 92.41 | 4,620,500 | 6.66 | 0.76 |
| Pos Control | | | | |
| Pos Control | 9.80 | 490 | 2.69 | 4.73 |
| Neg Control | | | | |
| Neg Control | 523.27 | 26,163,500 | 7.42 | — |

[1] = Chlorhexidine acetate.
[2] = Means within row.

TABLE VI

Trial 2, Organism: Streptococcus agalactiae

| | | Count | Plate No. | | | | | | | | | |
|---|---|---|---|---|---|---|---|---|---|---|---|---|
| Treatment | Dilution | No. | 1 | 2 | 3 | 4 | 5 | 6 | 7 | 8 | 9 | 10 |
| 10% solids with 5% chx[1] | −3 | 1 | 2 | 0 | 0 | 1 | 0 | 0 | 0 | 2 | 8 | 0 |
| 10% solids with 5% chx | −3 | 2 | 3 | 0 | 0 | 0 | 0 | 0 | 0 | 9 | 3 | 0 |
| 2.5% acetic acid | −4 | 1 | 24 | 19 | 72 | 39 | 25 | 24 | 14 | 29 | 21 | 28 |
| 2.5% acetic acid | −4 | 2 | 17 | 12 | 69 | 40 | 15 | 49 | 22 | 27 | 23 | 19 |
| Pos Control | −1 | 1 | 80 | 9 | 28 | 57 | 251 | 392 | 404 | 2 | 1768 | 105 |
| Pos Control | −1 | 2 | 186 | 12 | 29 | 49 | 247 | 624 | 417 | 1 | 1697 | 121 |
| Neg Control | −4 | 1 | 230 | 245 | 170 | 331 | 338 | 252 | 153 | 212 | 173 | 187 |
| Neg Control | −4 | 2 | 187 | 285 | 188 | 210 | 277 | 216 | 198 | 236 | 189 | 173 |

| Treatment | Geometric Mean | Total organisms Recovered | Log | Log reduction |
|---|---|---|---|---|
| 10% solids with 5% chx[1] | | | | |
| 10% solids with 5% chx | 0.074[2] | 370 | 2.57 | 4.47 |
| 2.5% acetic acid | | | | |
| 2.5% acetic acid | 25.98 | 1,299,000 | 6.11 | 0.93 |
| Pos Control | | | | |
| Pos Control | 87.61 | 4,380 | 3.64 | 3.40 |
| Neg Control | | | | |
| Neg Control | 217.18 | 10,859,000 | 7.04 | — |

[1] = Chlorhexidine acetate.
[2] = Means within row.

TABLE VII

Trial 3, Organism: Streptococcus agalactiae

| | | Count | Plate No. | | | | | | | | | |
|---|---|---|---|---|---|---|---|---|---|---|---|---|
| Treatment | Dilution | No. | 1 | 2 | 3 | 4 | 5 | 6 | 7 | 8 | 9 | 10 |
| 10% solids with 5% chx[1] | −4 | 1 | 94 | 131 | 190 | 95 | 140 | 57 | 123 | 127 | 141 | 143 |
| 10% solids with 5% chx | −4 | 2 | 105 | 163 | 191 | 108 | 138 | 53 | 128 | 130 | 117 | 193 |

TABLE VII-continued

Trial 3, Organism: Streptococcus agalactiae

| 10% solids without chx | -4 | 1 | 118 | 116 | 115 | 158 | 125 | 101 | 138 | 161 | 148 | 131 |
| 10% solids without chx | -4 | 2 | 98 | 140 | 126 | 191 | 151 | 124 | 126 | 122 | 173 | 108 |
| Neg Control | -4 | 1 | 221 | 84 | 243 | 115 | 192 | 120 | 102 | 132 | 186 | 1264 |
| Neg Control | -4 | 2 | 194 | 168 | 145 | 127 | 167 | 168 | 136 | 131 | 212 | 822 |

| Treatment | Geometric Mean | Total organisms Recovered | Log | Log reduction |
|---|---|---|---|---|
| 10% solids with 5% chx[1] | | | | |
| 10% solids with 5% chx | 122.10[2] | 6,105,000 | 6.79 | 0.17 |
| 10% solids without chx | | | | |
| 10% solids without chx | 131.53 | 6,576,500 | 6.82 | 0.14 |
| Neg Control | | | | |
| Neg Control | 184.00 | 9,200,000 | 6.96 | — |

[1] = Chlorhexidine acetate.
[2] = Means within row.

Microscopic Study of Microbial Culture on Coatings of the Invention

Two randomly chosen peelings from each experiment for Trials 1 and 2 were processed for light microscopic examination, specifically to observe for the presence of challenge microorganisms. A 4-mm$^2$ section of the coating film was excised from each peeling and fixed to the surface of a microscope slide by gentle heating. Gram stain was applied to detect the presence of Gram-positive bacteria.

Gram-positive cocci resembling staphylococci or streptococci were only rarely observed embedded in, or adhering to, the coating preparations, suggesting that the physical removal of the film with cotton swabs was not responsible for the reduction in bacterial numbers in rinses. Likewise, the plating of two randomly chosen entire peelings by swirling the coatings on selective media resulted in the growth of insignificant cfu of *Staph. aureus* or *Strep. agalacfiae*.

Therefore, physical removal of the PVDF/acrylic copolymer coatings played a minor role in stripping viable bacteria from the teat surface after challenge.

The foregoing is considered as illustrative only of the principles of the invention. Further, since numerous modifications and changes will readily occur to those skilled in the art of veterinary treatment, it is not desired to limit the invention to the exact method shown and described, and accordingly, all suitable modifications and equivalents may be resorted to, falling within the scope of the invention.

What is claimed is:

1. A method of prevention or treatment of bovine mastitis by forming a thin, flexible microporous breathable and strippable polymer coating having a physiologically active agent incorporated therein which is effective against mastitis-causing organisms, comprising the steps of:
   A. applying a film-forming composition to the teats of the udders, said composition comprises:
      (a) about 5 to 25 percent based on the weight of the total composition of a film forming mixture of
         (1) about 30 to 60 weight percent of solids of a polymer of polyvinylidene difluoride;
         (2) about 10 to 25 weight percent of solids of an acrylic aqueous emulsion whereby water is provided; and
         (3) about 10 to 30 weight percent of solids of an amine substituted acrylic polymer;
      (b) about 5 to 40 weight percent of solids of a physiologically active agent; and
      (c) about 85 to 95 weight percent of acetone so as to form two liquid phases; and
   B. Allowing said acetone and water from the applied film-forming composition to evaporate and form a thin, flexible adherent, pinhole-free phase inversion barrier film on the cutaneous tissue of the teat.

2. The method of claim 1, wherein said polymer of polyvinylidene difluoride is selected from homopolymers and copolymers thereof.

3. The method of claim 1, wherein said acrylic aqueous emulsion is selected from the group consisting of a copolymer of methyl methacrylate, butyl acrylate and acrylic acid, a copolymer of propyl methacrylate, butyl acrylate and acrylic acid, a copolymer of methoxyethyl methacrylate, butyl acrylate and acrylic acid, and a copolymer of methyl methacrylate, 2-ethylhexyl acrylate and methacrylic acid, and mixtures thereof.

4. The method of claim 1 wherein said amine-substituted acrylic polymer is prepared from monomers selected from N,N-dimethyl amin-ethyl (meth)acrylate, N,N-diethylaminoethyl (meth)acrylate, butyl-aminoethyl (meth) acrylate and the biologically active salts thereof.

5. The method of claim 1, comprising means for detecting pinholes in the formed film.

6. The method of claim 5, said pinhole detecting means comprises a colorant or dye.

7. The method of claim 1, wherein said polar organic solvent is acetone.

8. The method of claim 1, wherein said applying is by painting, spreading, swabbing, dipping or spraying.

9. The method of claim 1, wherein said applying step is by dipping.

10. The method of claim 8, wherein the teats are treated by being dipped in said film-forming coating at least once daily during the lactation period to form a barrier film 0.010 mm to 0.015 mm thick.

11. The method of claim 1, wherein said physiologically active agent is selected form the group consisting of antibiotics, disinfectants, antimicrobials, anti-inflammatory agents, antiphlogestics, hemostatics, cytostatics and hormones.

12. The method of claim 11, wherein said antimicrobials are selected from the group consisting of iodophors, chlorophenols, biquanides and the biologically active salts thereof.

13. The method of claim 12, wherein said antimicrobial is chlorhexidene diacetate.

14. The method of claim 1, further comprising the step of stripping the film coating by immersing the coated teat into an acetic acid solution followed by mechanical removal.

* * * * *